United States Patent
Seghatol

(10) Patent No.: US 7,004,755 B2
(45) Date of Patent: *Feb. 28, 2006

(54) HAND-HELD MICROWAVE INTRA-ORAL DENTAL SYSTEM

(75) Inventor: Marc Seghatol, 750 Monpellier Street 216, St. Laurent, Quebec (CA) H4L 5A7

(73) Assignee: Marc Seghatol, (CA)

( * ) Notice: Subject to any disclaimer, the term of this patent is extended or adjusted under 35 U.S.C. 154(b) by 519 days.

This patent is subject to a terminal disclaimer.

(21) Appl. No.: 09/897,317

(22) Filed: Jul. 2, 2001

(65) Prior Publication Data

US 2002/0106605 A1    Aug. 8, 2002

Related U.S. Application Data

(63) Continuation of application No. 09/399,580, filed on Sep. 20, 1999, now Pat. No. 6,254,389.

(30) Foreign Application Priority Data

Sep. 18, 1998   (CA) .................................... 2246663

(51) Int. Cl.
*A61C 5/00* (2006.01)
(52) U.S. Cl. .................................................. 433/215
(58) Field of Classification Search ................ 433/215, 433/224; 600/589, 590; 606/41; 607/101
See application file for complete search history.

(56) References Cited

U.S. PATENT DOCUMENTS

| 4,527,560 A | 7/1985 | Masreliez |
| 4,873,269 A | 10/1989 | Nakazato |
| 4,971,735 A | 11/1990 | Uebayashi |
| 5,026,959 A * | 6/1991 | Ito et al. |
| 5,147,903 A | 9/1992 | Podszun et al. |
| 5,151,279 A | 9/1992 | Kimura |
| 5,175,008 A | 12/1992 | Ueno |
| 5,207,231 A * | 5/1993 | Fakhri |
| 5,218,070 A | 6/1993 | Blackwell |
| 5,302,104 A | 4/1994 | Ueda |
| 5,324,186 A | 6/1994 | Bakanowski |

(Continued)

FOREIGN PATENT DOCUMENTS

CA          2120880          10/1995

(Continued)

OTHER PUBLICATIONS

Feilzer AJ et al., "Curing contraction of composites and glass-ionomer cements," *Journal of Prosthetic Dentistry*, vol. 59, pp. 297-300 (1988).

(Continued)

*Primary Examiner*—Ralph A. Lewis

(57) ABSTRACT

A hand-held microwave system for intra-oral dentistry utilizes microwave energy to cure polymer materials intra-orally so as to produce dental composites having improved physical characteristics, and also utilizes microwave energy to detect the presence of and to preferentially heat caries or cavities, thereby disinfecting and therapeutically treating the caries in a potentially non-invasive manner. The intra-oral polymerization process can be accomplished with less overall energy and with composite-matrices that maximally absorb the microwave energy so as to reduce heating of adjacent tissue. The antenna of a hand-held version of the intra-oral microwave system is also advantageously designed to detect the presence of and to preferentially heat caries or cavities, thereby disinfecting and therapeutically treating the caries in a potentially non-invasive manner. A method and product by process for the system are also disclosed.

7 Claims, 7 Drawing Sheets

U.S. PATENT DOCUMENTS

| | | | |
|---|---|---|---|
| 5,358,515 A * | 10/1994 | Hurter et al. | 607/101 |
| 5,421,727 A | 6/1995 | Stevens et al. | |
| 5,456,603 A * | 10/1995 | Kowalyk et al. | 433/215 |
| 5,502,087 A | 3/1996 | Tateosian et al. | |
| 5,510,411 A | 4/1996 | McKinstry et al. | |
| 5,645,748 A | 7/1997 | Schiffmann et al. | |
| 5,893,713 A | 4/1999 | Garman et al. | |
| 6,033,401 A * | 3/2000 | Edwards et al. | 606/41 |
| 6,036,494 A * | 3/2000 | Cohen | 433/215 |
| 6,083,218 A * | 7/2000 | Chou | 606/10 |
| 6,254,389 B1 * | 7/2001 | Seghatol | 433/215 |

FOREIGN PATENT DOCUMENTS

| | | |
|---|---|---|
| CA | 2148536 | 11/1995 |
| EP | 0 193 514 B1 | 8/1990 |
| EP | 0 687 451 A2 | 12/1995 |
| JP | 7031632 A | 2/1995 |

OTHER PUBLICATIONS

Ferracane JL et al., "Wear and marginal breakdown of composite with various degrees of cure," *J Dent. Res.*, vol. 76, No. 8, pp. 1508-1516 (1997).

Hayden WJ, "Flexure strength of microwave-cured denture baseplates", *General Dentistry*, vol. 343, pp. 367 (1986).

Al Doori D et al. "A comparison of denture base acrylic resins polymerised by microwave irradiation and by conventional water bath curing systems," *Dental Materials*, vol. 4, pp. 25-32 (1988).

Geerts G et al., "A comparison of the bond strengths of microwave and water bath-cured denture materials," *The Journal of Prosthetic Dentistry*, vol. 66, No. 3, pp. 403-407 (Sep. 1991).

Turck MD et al, "Microwave processing for dentures, relines, repairs and rebases," *The Journal of Prosthetic Dentistry*, vol. 69, No. 3, pp. 340-343 (1993).

Wallace PW et al., "Dimensional accuracy of denture resin cured by microwave energy," *The Journal of Prosthetic Dentistry*, vol. 68, pp. 634-640 (1992).

Salim S. et al. "The dimensional accuracy of rectangular acrylic resin specimens cured by three denture base processing methods," *The Journal of Prosthetic Dentistry*, vol. 67, pp. 879-885 (1992).

Ferracane JL, "Elution of leachable components from composites," *Journal of Oral Rehabilitation*, vol. 21, pp. 441-452 (1994).

Hume WR et al., "Bioavailability of components of resin-based materials which are applied to teeth," *Crit. Rev. Oral Biol. Med.*, vol. 7, No. 2, pp. 172-179 (1996).

Urabe H. et al. in "Influence of polymerization initiator for base monomer on microwave curing of composite resin inlays," *Journal of Oral Rehabilitation*, vol. 26, pp. 442-446 (1999).

"The Prosthoflex automated injection system from ATP Industries, Inc." *Dental Lab Products*, Sep./Oct. 1995, pp. 14.

N. Hoshi et al in "Application of Microwaves and Millimeter Waves for the Characterization of Teeth for Dental Diagnosis and Treatment," *IEEE Transactions on Microwave Theory and Techniques*, Jun. 1998, vol. 46, No. 6, pp. 834-838.

* cited by examiner

70

HAND-HELD MICROWAVE INTRA-ORAL DENTAL SYSTEM

This is a Continuation of U.S patent application Ser. No. 09/399,580 filed Sep. 20, 1999, now U.S. Pat. No. 6,254,389.

FIELD OF THE INVENTION

The present invention relates generally to the field of dentistry. More specifically, the present invention relates to a hand-held microwave system for intra-oral dentistry that utilizes microwave energy to cure polymer materials intra-orally so as to produce dental composites having improved physical characteristics, and also utilizes microwave energy to detect the presence of and to preferentially heat caries or cavities, thereby disinfecting and therapeutically treating the caries in a potentially non-invasive manner.

BACKGROUND OF THE INVENTION

The use of polymer materials in the dental arts for the restoration of lost or damaged teeth is well known. Such uses fall into two general categories: (i) the use of polymer materials to produce dental prosthetics, such as dentures, bridges and crowns, that are either permanent or removable articles, and (ii) the use of polymer materials to create dental composites for fillings to repair teeth instead of using conventional amalgam fillings or as veneers to refinish tooth enamel surfaces. The first category of dental articles, dental prosthetics, are created outside of the patient (i.e., extra-oral), typically by making an impression of what the desired article should look like and then molding the article to match the impression. The second category of dental articles, dental composites, are created directly in the patient's mouth (i.e., intra-oral) as fillings or veneers to repair or resurface teeth.

The use of microwave energy in the form of a commercial microwave oven used to process dental prosthetics extra-orally is well known. Various types of flasks and molding equipment that can be used in conjunction with a commercial microwave oven for processing and curing dental articles made of polymers have been developed as described, for example, in U.S. Pat. Nos. 4,971,735, 5,151,279, 5,324,186 and 5,510,411, European Patent No. 0 687 451 A2 and Japanese Patent No. JP7031632A. Examples of polymer resin matrices that are specifically formulated to utilize microwave energy supplied by a commercial microwave oven for the thermal polymerization of the polymers into dental articles are shown in U.S. Pat. Nos. 4,873,269, and 5,218,070 and Canadian Patent No. 2,148,436. The impact of the role played by the polymer initiator in a microwave cured resin matrix has been evaluated by Urabe H. et al. in "Influence of polymerization initiator for base monomer on microwave curing of composite resin inlays," *Journal of Oral Rehabilitation*, Vol. 26, pp. 442–46 (1999). The repair of dentures and related articles using microwave processing is also described in Turck M D et al, "Microwave processing for dentures, relines, repairs and rebases," *The Journal of Prosthetic Dentistry*, Vol. 69, No. 3, pp. 340–43 (1993). Generally, dentures cured by commercial microwave ovens have improved mechanical properties, and often have better adaptation than those cured by conventional water-bath method. The primary advantage of microwave curing, however, is the reduced processing times which can be shortened from 8 hours or more to as little as a few minutes.

There has been relatively little research, however, into the potential impact of the microwave energy itself on the polymerization process for dental prosthetics. The research that has been done has generally focused on the duty cycle used for the microwave oven curing process. The impact on porosity of denture material cured using lower wattage, longer duration microwave cure times (i.e., a lower duty cycle for a longer time) versus higher wattage, shorter duration microwave cure times (i.e., a higher duty cycle for a shorter time) is compared in Alkhatib M B, et al. "Comparison of microwave-polymerized denture base resins," *The International Journal of Prothodontics*, Vol. 3, No. 2, pp. 249–55 (1990). European Patent No. 0 193 514 B1 describes a microwave processing system for dental prosthetics that has a magnetron, a waveguide, a surface radiating antenna, a flask, and a temperature sensor that is inserted in the flask and connected to a regulating processor. The regulating processor limits the temperature in the flask as measured by the temperature sensor by turning on and off the magnetron based on frequency modulation of the duty cycle. Although not used for polymerization of dental articles, U.S. Pat. No. 5,645,748 does describe a microwave system for sterilization that controls duty cycle of a microwave oven for the purpose of minimizing arcing caused by metallic surgical or dental instruments.

With respect to the second category of dental articles created using polymer materials, dental composites formed of polymer matrix-composites are increasingly being used as an alternative to mercury-containing dental amalgam for aesthetic and restorative dental materials. These kinds of polymer matrix-composites are usually photo polymerizable in that they are cured using some kind of light instead of heat. Generally, the polymer matrix-composite is based on a photo polymerizable polyfunctional methacrylate compound that can be used alone or as a mixture with monomethacrylates, light sensitive cure initiators pigments and fillers in a mixture with various comonomers such as triethyleneglycol dimethacrylate. Although the half-life of these polymer matrix-composites cured by light is on the order of 5–8 years and therefore they tend to wear out earlier than conventional dental amalgams, the enhanced biofunctionalilty and more pleasing aesthetic qualities of these polymer matrix-composites have gained favor over conventional dental amalgams.

The main deficiencies of polymer composite resins used as dental composites are surface degradation which leads to inadequate wear resistance, polymerization shrinkage and a lack of density. In addition to the problems previously described for dental prosthetics, micro-shrinkage of polymer dental composites produces interfacial gaps on the surface of the composites, which can result in microleakage through the dental composite. The long-term consequence of such microleakage can be bacterial penetration into the tooth that can cause a variety of adverse reactions such as pulp damage, tooth sensitivity, possible pulpal death and loss of adhesion of the dental composite.

Improving the degree of polymerization of polymer matrix-composites is generally considered to be one way of improving their physical and biofunctionality characteristics of polymer dental composites as this would lead to stronger dental composites that are less susceptible to degradation, wear and fracture. It would also lead to improved biocompatibility, since there would be reduced amounts of uncured monomer that could act as a biohazard.

Unlike polymer dental prosthetics, however, the curing of polymer matrix-composites by application of thermal energy generally has not been used to date. Obviously, in the case of the conventional thermal water-bath process, it would be impractical to require a patient to remain at the dentist's office for up to 8 hours with their mouth open and with a tooth immersed in a hot water bath in order to set a thermally polymerizable matrix-composite. It is also not possible to place a patient's mouth into a commercial microwave oven to set a thermally polymerizable matrix-composite.

While there are numerous hand-held medical catheter devices that utilize radio frequency and microwave energy to perform ablations and similar heating operations, for example, in the vascular system of a patient, there have been relatively few uses of thermal or electrical energy applied to hand-held dental tools for intra-oral applications. There have been a few hand-held dental probes that utilize an electrically resistive heated tip for diagnosis of dental decay or for melting a sealing material in an intra-oral context as described, for example, in U.S. Pat. Nos. 4,527,560 and 5,893,713. U.S. Pat. No. 5,421,727 describes the use of radio frequency/microwave energy as part of a hand-held endodontic root canal device to raise the temperature of the interior of the tooth adjacent to the root canal, thereby tending to disinfect the tooth during the root canal procedure as a result of the increased temperature.

The extra-oral use of microwave energy for the purpose of characterizing dental decay in extracted teeth has been described by N. Hoshi et al in "Application of Microwaves and Millimeter Waves for the Characterization of Teeth for Dental Diagnosis and Treatment," *IEEE Transactions on Microwave Theory and Techniques*, Jun. 1998, Vol. 46, No. 6, pp. 834–38. This study confirmed the higher absorbency behavior of carious lesions in extracted teeth when irradiated by microwave energy as compared to the lower absorbency of such microwave energy by healthy enamel and dentin.

While existing photo polymerizable dental composites have enjoyed success as compared to conventional dental amalgams for dental fillings and veneers, it would be desirable to further improve the uniformity and degree of conversion of monomers into polymer chains in the polymerization process in order to produce even better dental composites. It would also be desirable to provide a dental tool that could take advantage of the use of microwave energy for purposes other than the polymerization of dental composites.

SUMMARY OF THE INVENTION

The present invention is a hand-held microwave system for intra-oral dentistry that utilizes microwave energy to cure polymer materials intra-orally so as to produce dental composites having improved physical characteristics, and also utilizes microwave energy to detect the presence of and to preferentially heat caries or cavities, thereby disinfecting and therapeutically treating the caries in a potentially non-invasive manner. The intra-oral polymerization process can be accomplished with less overall energy and with composite-matrices that maximally absorb the microwave energy so as to reduce heating of adjacent tissue. The antenna of a hand-held version of the intra-oral microwave system is also advantageously designed to detect the presence of and to preferentially heat caries or cavities, thereby disinfecting and therapeutically treating the caries in a potentially non-invasive manner.

The hand-held dental tool is designed to apply continuous microwave energy in accordance for use in creating dental composites directly in a patient's mouth. Microwave energy having a frequency of between 1 GHz to 50 GHz, and preferably between 14 GHz to 24 GHz, is applied by an antenna at the distal end of the hand-held tool which is connected via a conductor or wave guide to a microwave generator that supplies low power microwave energy in response to precisely controlled voltages. Preferably, the microwave energy power is less than about 10 W and ideally between 3 W and 5 W and the control voltages operate between 12 V and 65 V, depending upon the desired curing time and the particular composition of the resin matrix to be cured. Preferably, the antenna and distal end of the hand-held tool are structured to enable the operator to exert some degree of pressure on the composite resin-matrix in the mouth while it is being cured by the application of microwave energy. The low power microwave energy provided by the hand-held tool of this embodiment is safe for intermittent human exposure as the power and frequency ranges emitted by the antenna are similar to that emitted by cellular telephones.

One of the advantages of the hand-held dental tool is that it can also serve as a tool for non-invasively detecting and/or treating caries or cavities. Carious tooth tissue consists of demineralized and softened and moist tooth enamel or dentin, and contains micro-organisms. If the carious tooth tissue has not degraded to the point where the physical properties of the tooth are compromised, it is possible for the carious tooth tissue to recalcify and reharden if the micro-organisms causing the carious tooth tissue can be killed and the tooth can be kept under aseptic conditions. Infected tooth tissue which is not removed or not kept under aseptic conditions will remain as an active carious lesion, and will continue to cause progressive and destructive loss of tooth tissue. The use of the continuous microwave energy supplied by the hand-held dental tool embodiment of the present invention can eliminate or reduce the infection caused by the micro-organisms as the type of microwave energy is selected to preferentially heat and destroy the micro-organisms in the carious tooth tissue. In some cases, the hand-held dental tool can be used to kill the micro-organisms internal to the tooth tissue by the use of microwave energy and then a sealant can be applied to the exterior of the tooth which will be sufficient to keep an aseptic environment and promote the recalcification of the underlying tooth tissue. In other cases, portions of the carious tooth tissue may need to be removed and the hand-held tool can be used to kill the micro-organisms both internal to the tooth tissue and on the surface of the cavity. Once the micro-organisms have been destroyed, a polymer dental composite can be applied to the cavity. The polymer dental composite is preferably microwave cured using the hand-held dental tool to seal the treated tooth tissue and provide additional physical and structural support for the cavity.

DETAILED DESCRIPTION OF THE PREFERRED EMBODIMENT

Figure 1:
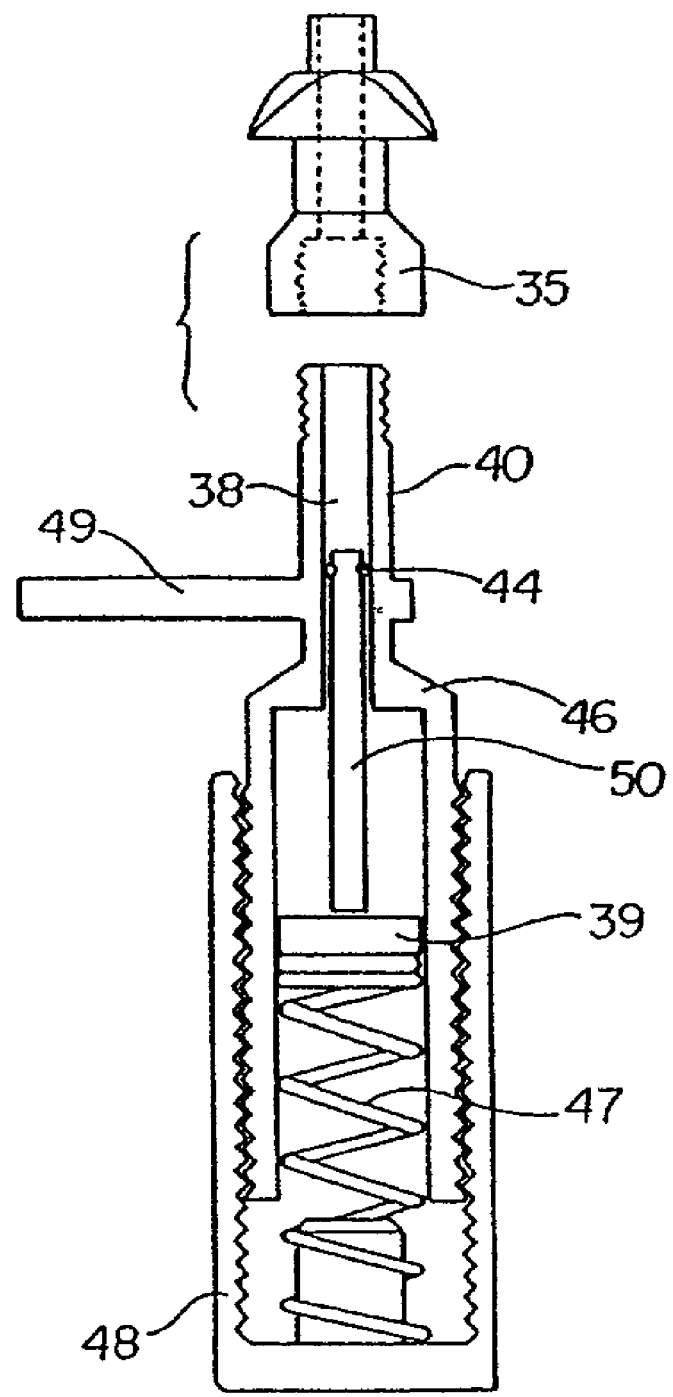
FIG. 1 is a partial cross-sectional side view showing the details of a preferred embodiment of the polymer material injector system.

Referring now to the various figures, a detailed description of the preferred embodiment of the present invention will be presented. Various complex dielectric permittivity, temperature and distribution pattern studies of microwave heated teeth and simulations of specific absorption rate distribution have been conducted as part of the research into the present invention. The complex permittivity was measured on different types of dental tissues, using extracted teeth, including enamel, dentin and caries. Reflective coefficients have been obtained using a network analyzer. The characteristics of enamel caries and dentin are different. The dielectric loss factor of caries is fairly higher than that of normal healthy parts particularly in the millimetric wave in the frequency between 12 GHz to 25 GHz. When the tooth is exposed to millimetric microwaves in this range, caries are preferentially heated. Temperature rise can kill the microorganisms in caries. Control and/or extinction of microorganism slows or stops the progress of caries, permitting previously carious tissue to recalcify by biological latent support of the pulp. Temperature distribution measurement with microwave heating reveals that the temperature of caries is higher than that of normal tooth tissue. These properties are used with the provisions of this invention for the diagnostic and treatment of teeth having caries and subsequent internal heat conditioning and/or curing of provided dental restorative materials. When dielectric loss factor is higher, the absorption of microwave is better and local temperature is higher. Microwave energy heats by radiation and is able to penetrate through various substances including desiccated tissue and thus can create an addressed effect.

To understand the details on which the preferred embodiment is based, it is helpful to understand how microwave energy is generated and absorbed. The microwave energy absorbed by a given dental material is governed by the following equation:

$$P = 2\pi f E^2 \epsilon' \tan \delta$$

where:
P=Power density (w/m$^3$)
f=frequency
E=electrical field strength (rms)
$\epsilon'$=dielectric constant of the dental material
tan $\delta$=dielectric loss factor.

This equation shows that in order to determine the microwave energy in terms of the incident microwave power level absorbed by a dental article, both the applied electric field strength and the dielectric material characteristics must be known. One of the difficulties in properly evaluating this equation is that when a curable dielectric resinous material is polymerized, its microwave absorption is drastically reduced because the dielectric constant of the material changes as a result of the polymerization process. Similarly, when microwave energy is directed to a tooth containing a carious lesion, the absorption of the microwave energy changes. The present invention utilizes this difference in absorption as a mechanism for identifying carious lesions with the same hand-held dental tool that can be used to non-invasively treat those caries.

Figure 2:
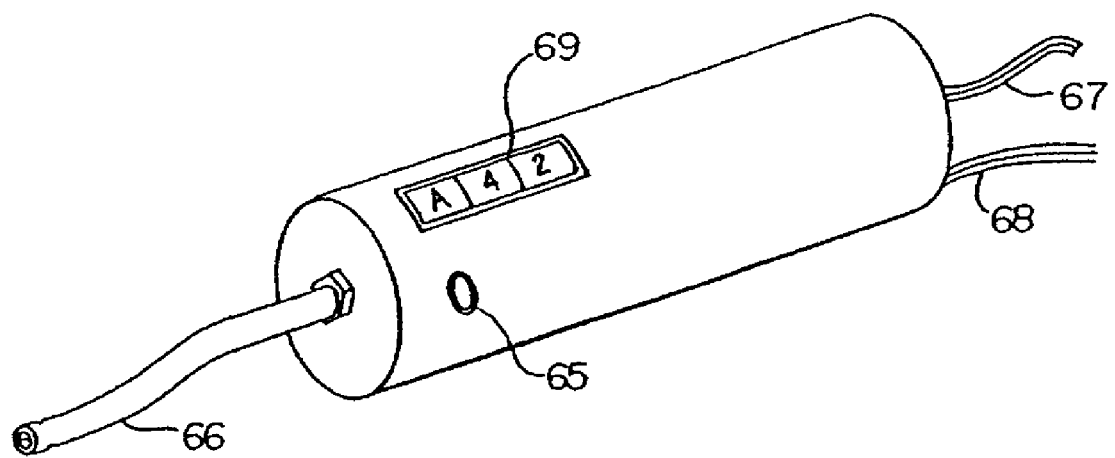
FIG. 2 is an isometric view of a hand-held dental tool embodiment of the present invention.
Figure 7:
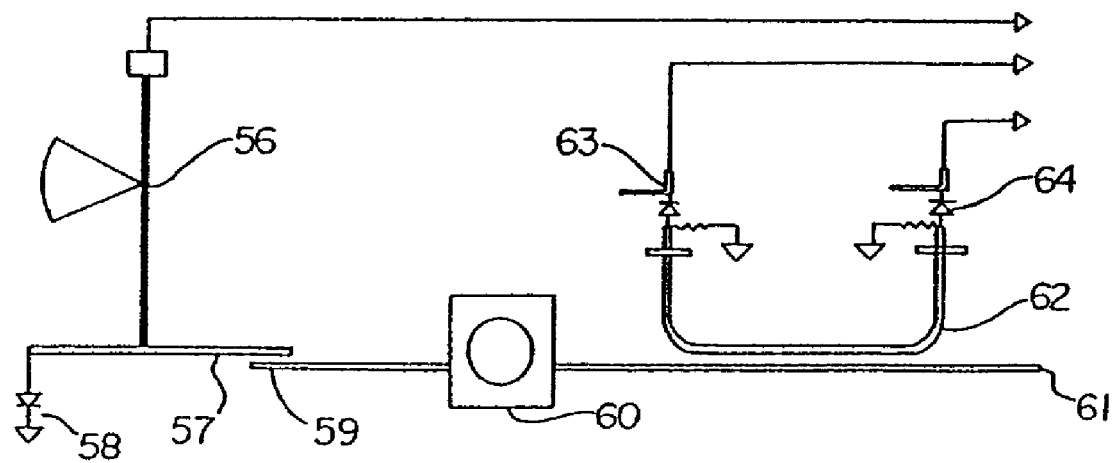
FIG. 7 is an electrical schematic of the control circuitry for generating the microwave energy in the hand-held dental tool embodiment shown in FIG. 2.

In one embodiment as shown in FIG. 7, a system of caries control in a non-invasive atraumatic way, without surgical burs entry and with a reduced risk and necessity of exposing the dental pulp organ comprise, a hand-held microwave applicator with a sufficient microwave power delivery capability is provided to heat the dental tissues or restorative materials. The electronic circuit diagram of FIG. 7 is designed to suit small microwave generators such as an oscillation source coupled with a RF power amplifier or impatt diodes or similar solid state or transistorized microwave emitters with an output power of about 2 to 5 watts which requires usually an electrical voltage of about 60 DC. The bias voltage is applied through a high impedance line (56) in order to limit the perturbation of electromagnetic signals. A power supply module is provided with a current and voltage limiting means to permit the polarization of the impatt diode in the specific limits with a resonant circuit (57), such as a 50 ohms line, having a length preferably equal to the half of the length of the selected frequency. The length of the line may be calculated with the following equation: $L = 3 \times 10^8 / 2f_{\mathit{eff}}^{1/2}$. One end of the "resonator" is connected to the impatt diode (58) and the other end of it is coupled (59) to a transmission line including an isolator (60) to provide isolation of the microwave source from the rest of the circuit in order to avoid frequency variations, caused by a mismatch of the output (61). A coupler (62) having a coupling of about −15 dB permit a sampling of the signal emitted by the microwave generator in order to measure the incident and reflected power levels. The couplers should be perfectly matched at both extremities to permit precise measurements. Matching circuit (63) at the input and the output as well as load resistors permit achievement of an adaptation at each end, equal or better than −15 dB. Detecting diodes (64) rectify the radio frequencies signal in order to convert the power to a dc voltage which can advantageously be subsequently transmitted to a micro controller or a "ADC" analog digital converter which converts this voltage to a digital signal for an appropriate processing of the acquired information and the precise monitoring and the control of the microwave's energy delivered to the dental target. The controller is a means of setting the power level, exposure cycles, processing modes, and may also be used in the selection of the frequency of microwave generation. As shown in FIG. 2, the control of the microwave source is preferably made by a selector (65), located on the device, allowing the operator to set different power levels and modes. Between the tip antenna and the microwave source or amplifier, a shielded cable (66) or wave guide, as short as possible is used to operatively transmit the microwave power to the head antenna.

A suitable connector preferably permits the interchange of different provided head antennas to match different applications and enhance energy transmission and deposition on the dental target. A means of electrical supply (67), such as a shielded cable, connects the mobile applicator to the power supply. The hand-held applicator may be equipped with a water cooling system (68) and a digital display (69).

Figure 4:
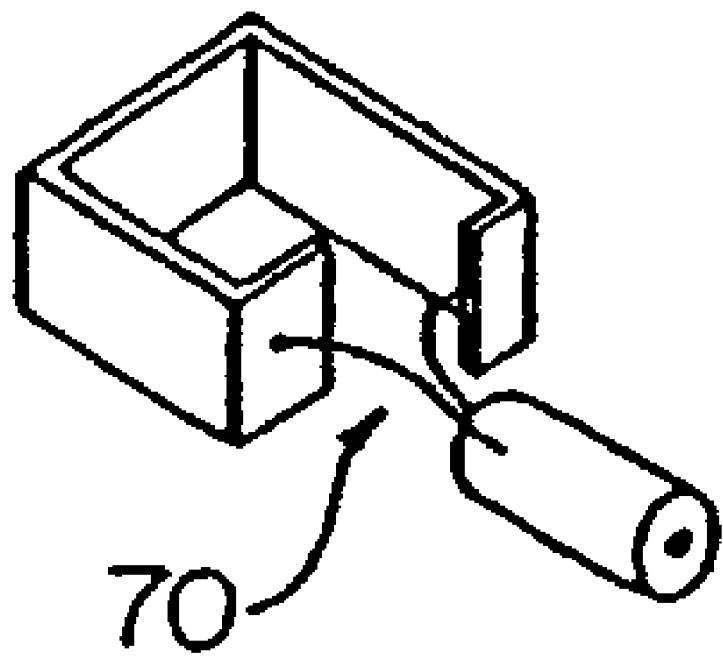

One head antenna (70), as shown in FIG. 4, is provided for therapeutic purposes to target teeth and treat, heat or detect dental caries, and is made of a highly conductive metal such as copper, platinum or gold, plated or not, having the format of a rectangular or a loop-shaped band, of which one end is connected to the inner and the outer conductors of the transmission line.

Figure 5:

One provided monopole head antenna has the form of an I as shown in FIG. 5. This applicator is made for example by stripping the outer jacket and the outer conductor of a coaxial shielded cable, the inner conductor and dielectric (Teflon) constitute the applicator. To increase the directivity of the radiating microwave energy, a loaded I-applicator (71) having an increased forwarding effect may be made by placing a platinum ring over the outer conductor of the coaxial cable and soldering a platinum rod on the inner conductor of the antenna.

Figure 6:
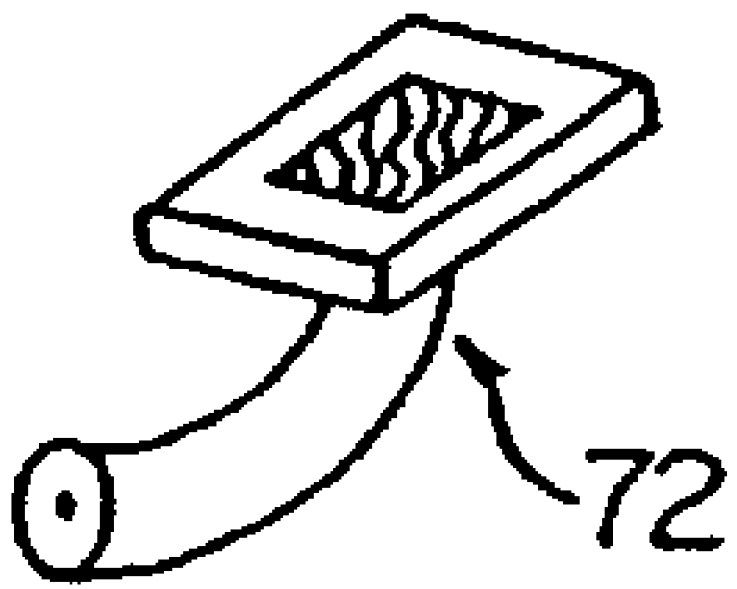

Another provided head antenna (72), as shown in FIG. 6, is made of a microstrip, which may be made of miscible polymeric or other conductive materials, having the format, for example, of a square metal skin is positioned on a dielectric substrate with a ground plane on its back.

An electrically shielded temperature probe may be embedded in the head of the hand-held applicator antenna to provide a means of monitoring the temperature of the heated target for judging the efficiency of tissue heating and to avoid sudden temperature rises.

Figure 3:
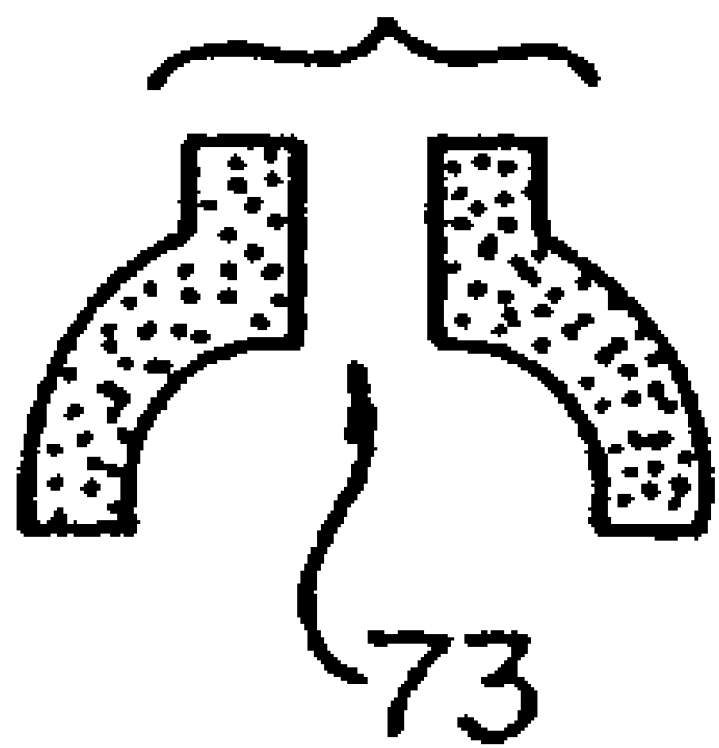
FIGS. 3–6 are various embodiments of antennas for the distal end of the hand-held dental tool embodiment of FIG. 2.

The provided head antenna designs help in achieving good impedance matching and effective delivery of microwave for internal heat conditioning of dental targets. As shown in FIG. 3, a means of safely containing any leakage of microwave energy close to the irradiation space can be used such as the disclosed head antenna choke (73), made of microwave absorbing materials.

Preferably, the antennas are made with a portion that is strong and flexible enough to be used as a positioning and compression tool for the pasty resin matrix for the dental composite. The loop and patch antenna may preferably carry negative dental molds to aid in the formation of the dental composite. Alternatively, a miniaturized version of a manual resin injector, such as previously described in connection with FIG. 1, may be provided to deliver the pasty resin matrix for the dental composite as part of the hand-held tool. While the hand-held tool is preferably used in an intra-oral application with dental composites, it will be recognized that the hand-held tool can also be used in the dental office, for example, to accomplish repairs or welds of dental prosthetics devices as well.

In one embodiment as shown in FIG. 1, an economic manual fluid resin pressurization and injection device (46) is provided to remove the need of being connected to an external pressurized fluid source. A mechanical force accumulator such as a spring (47) is compressed by turning the internally threaded cylinder (48) while holding the device handle (49). A force boosting piston (50) is especially useful for molding and filling of composite curable dental materials. The injection nozzle and the piston acts as previously described. This embodiment can be miniaturized and employed with the hand-held intra-oral microwave applicator.

In general, various polymer based material compositions are useful for the construction of dental devices. These compositions may be used in the filling of teeth and the construction of appliances used for replacing teeth and other oral structures.

One preferred composition for dental composites suited to be formed and hardened in accordance with the providing of this invention consists of a polymerizable mixture including one or a selection from the large family of polyfunctional methacrylate esters, and oligomers including the compound prepared from one molecule of bisphenol A and two molecules of glycidyl methacrylate called 2,2bis[4(2-hydroxy-3 methacryloyloxy-propyloxy)-phenyl] propane, known as Bis-GMA for its lower degree of shrinkage and/or 2,2-bis [4-methacryloxyethoxy)Phenyl] propane for its good water resistance properties. Other monomers, such as triethyleneglycol dimethacrylate for viscosity reduction, urethane dimethacrylates, spiro orthocarbontes, etc. are advantageously employed in admixture with silanized inorganic fillers and organic fillers, coupling agents, microwave sensitive cure initiation system including organic peroxides and amines and color pigments are advantageously added. The weight of the fillers as an overall weight of the composite is preferably in the range of 30 to 90% and include silanized silicon dioxide particles.

In one embodiment, compositions specially suitable for making dental removable appliances such as dentures is provided which comprise a liquid and a powdery component. The liquid component in accordance with the invention contains preferably from 40% to 90% of mono-, di-, tri, or multifunctional acrylic monomer, a cross-linking agent, a plasticizer, a stabilizer, an accelerator and color pigments. The mono-, di, tri, or multifunctional acrylic monomer in accordance with the invention are within the scope of the formula:

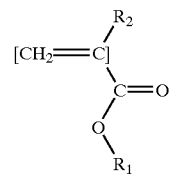

where R1 in accordance with the invention is hydrogen, alkyl, substituted alkyl group, cyclic hydrocarbon, benzyl, ether, hydroxyalkyl and R2 is hydrogen, halogen, alkyl, substituted alkyl or cyclic hydrocarbon group.

Monomers within the scope of the following formula are also particularly suitable to the invention:

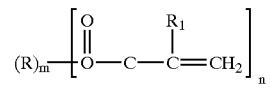

wherein R is an acrylic-free organic moiety, $R_1$ is hydrogen, hologen, halogen, alkyl, substituted alkyl or cyano radical and n is an integer from 1 to 20 and m is an integer from 1 to 1000. These monomers may be used alone or in admixture.

The microwave sensitive initiators in accordance with the invention include benzoyl and peroxide, dilauroyl peroxide up to 2.5%. The polymerization accelerator in accordance with the invention is a quaternary ammonium chloride, which is easily soluble in the methacrylate monomers and reacts with barbituric acid derivatives. A preferred compound is the quaternary ammonium with an alkyl of 1 to 20 carbons, such as, dodecyltrimethylammonium. These quaternary ammonium chlorides may be added in alone or in admixture from 0.09 to 1.5%. The cross-linking agent, in accordance with the provided microwave hardening material compositions, is a polyfunctional monomer wherein at least two carbon-carbon double bonds, such as 1,3-butanediol dimethacrylate, 1,4-butanediol dimethacrylate, 1,4-butanediol divinyl ether, di(ethylene glycol) dimethacrylate, di(ethylene glycol) divinyl ether, pentaerythritol diacrylate monostearate, ethylene glycol dimethacrylate, trimetylolpropane trimethacrylate, pentaerythritol triacrylate, pentaerythritol tetraacrylate, trimetylolpropane triacrylate. The cross-linking agents may be used alone or in admixture.

Polymerization promoters for the monomers of the provided curable material compositions for the present invention are useful because they rapidly react with the quaternary ammonium chloride to produce radicals, which promotes a rapid and uniform polymerization in the composition and a higher degree of conversion. The barbituric acid derivative in accordance with the invention include 1,3,5-trimethylbarbituric acid, 1,3-dimethyl-5-isobutylbarbituric acid, 1,3-dimethyl-5-phenylbarbituric acid, 5-n-butylbarbituric acid, 5-ethylbarbituric acid, 1-cyclohexyl-5-ethylbarbituric acid and 1-benzyl-5-phenylbarbituric acid. These acid derivatives may be used alone or in admixture in very small amounts. The polymerization stabilizers comprise hydroquinone, hydroquinone monomethyl ether or 4-ethoxyphenol which are usually added to the liquid component of dental compositions (up to 4%). The plasticizer in accordance with the invention is generally a low molecular weight ester, such as dibutyl phthalate or phosphates.

The composition for a one component microwavable curable material system in accordance with this invention is approximately the same as the one for the two component materials with some variations mainly in the initiation system. Preferred initiators, for a one component dental composition for denture or such, need to be thermally stable at room or higher temperatures such as 50$_i$C and initiate polymerization at higher temperatures such as benzopinacole, tert-butyleperbenzoate, and 2,2'dichlorobenzopinacol.

The powder component in accordance with the invention includes from 20% to 80% of mono-di-tri, or multifunctional acrylic or acrylate ester polymer. The powder may advantageously include from 5% to 40% of a copolymer. The powder component in accordance with the invention may advantageously include from 0.1% to 3% of an initiator for radical polymerization including organic peroxides such as benzoyl peroxide and dilauroyl peroxide. The powder component in accordance with the invention can include up to 1% of a barbituric acid derivative to promote chemical reaction. The mono-, di, tri, or multifunctional acrylic polymer used in denture base in accordance with the invention are:

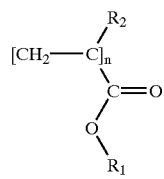

where the R1 in accordance with the invention is hydrogen, alkyl, substituted alkyl group, cyclic hydrocarbon, benzyl, ether, hydroxyalkyl, R2 is hydrogen, halogen, alkyl, substituted alkyl group and n is an integer at least equal to 2. The copolymer in accordance with this invention are mainly composed of methyl methacrylate polymer or a mixture of methyl methacrylate polymer and an methacrylate polymer other than methyl methacrylate polymer.

Inorganic and organic fillers may be added into the compositions of one or two components' denture base.

Useful inorganic fillers include glass, metal ceramics, silicon dioxide in powdery or fiber format, which are preferably silanized with a coupling agent, such as 3-methacryloxloxypropyltrimethoxy. Organic fillers include splinter or bead polymers of high molecular weight, or fibers such as aramide fibers, polyacrylate fibers, polyamide fibers and polyacrylonitrile fibers. Organic fillers may be used alone or mixed with inorganic fillers.

Thermoplastic compounds such as poly functional methacrylate, polycarbonate, polysulfone, fluoropolymers, elastomers, polyurethanes, impression compound, wax, gutta percha, polycaprolactone and mixtures of thermoset and thermoplastics are advantageously heat processed with the provided method and permit dental rehabilitation.

Microwave absorbing substances can advantageously be incorporated into disclosed thermoplastic and thermohardening material compositions, to decrease internal heat generation of compositions which does not have sufficient dielectrical loss when microwaved nor do they have sufficient heatability for a desired speed of heating. These microwave absorbents are also useful when the employed polymeric material has only a low microwave absorption behavior at low temperatures such as many thermoplastic polymers including polycarbonate and also for substantially increasing the speed and the addressability such as in welding and joining functions. These absorbers may be powdery, hollowed, coated and comprise ferromagnetics, metallic oxides or specialty ceramics. Microwave absorbent materials and/or sterilants can be advantageously utilized with the intra-oral embodiment of the present invention to increase the speed and addressability of heating the dental composite and to increase the effectiveness of the sterilization of the targeted caries.

The following tables set forth several examples in accordance with the various aspects of the present invention. All ratios for materials are expressed in weight.

Experiment of Decay Control in the Cavity Microwave Applicator

| | Preparation | Microwave irradiation | Incubation | Results |
|---|---|---|---|---|
| Section of decayous freshly extracted human teeth prepared, 2 mm³ | Surface desinection, 15 seconds deeping in cloramine T solution | 1.5 W/cm² energy density of irradiation (200 W in the cavity applicatior) 60 sec. | Culture of irradiated & non irradiated witness decayous teeth sections in a medium at 37$_i$C 24 h. | -Microwave irradiation destroy 80% carious zone microorganisms -Witness teeth cultures cloudy |

The invention claimed is:

1. A microwave dental system comprising:
    a hand-held dental tool including:
        an antenna positioned at a distal end of the tool and configured to be selectively positioned within a mouth of a patient adjacent at least one exterior surface of a tooth and including an antenna choke made of a microwave absorbing material; and
        a waveguide connected to the antenna; and a source of microwave energy operably coupled to the waveguide, including a control system for controlling delivery of microwave energy to the waveguide such that the dental tool delivers microwave energy to the at least one exterior surface of the tooth and the microwave energy is applied at a frequency and power to preferentially heat caries.

2. The microwave dental system of claim 1 wherein control system controls the source of microwave energy to deliver less than 10 W to the antenna.

3. The system of claim 1 wherein the control system operates the source of microwave energy at voltages in a range of between 10 and 65 V.

4. The system of claim 1 wherein the control system operates the source of microwave energy at frequencies of between 1 GHz to 50 GHz.

5. The system of claim 4 wherein the control system operates the source of microwave energy at frequencies between 14 GHz to 24 GHz.

6. The system of claim 1 wherein the control system includes a feedback sensor and the microwave energy is applied to allow the feedback sensor to detect caries.

7. A microwave dental system comprising:
 a hand-held dental tool including:
  an antenna positioned at a distal end of the tool and configured to be selectively positioned within a mouth of a patient adjacent at least one tooth, the antenna including an antenna choke to restrict transmission of microwave energy to surrounding tissue; and
  a waveguide connected to the antenna; and
 a source of microwave energy operably coupled to the waveguide, including a control system for controlling delivery of microwave energy to the waveguide.

* * * * *